(12) United States Patent
Kim et al.

(10) Patent No.: US 9,775,722 B2
(45) Date of Patent: Oct. 3, 2017

(54) CAGE HAVING SPIKE

(71) Applicant: LDR Medical, Rosières Près Troyes (FR)

(72) Inventors: Seo-Kon Kim, Gyeonggi-do (KR); Il Kim, Seoul (KR)

(73) Assignee: LDR Medical, Sainte-Savine (FR)

( * ) Notice: Subject to any disclaimer, the term of this patent is extended or adjusted under 35 U.S.C. 154(b) by 470 days.

(21) Appl. No.: 14/460,536

(22) Filed: Aug. 15, 2014

(65) Prior Publication Data
US 2015/0127107 A1    May 7, 2015

(30) Foreign Application Priority Data

Sep. 11, 2013   (KR) .......................... 10-2013-108840

(51) Int. Cl.
*A61F 2/44*    (2006.01)
*A61F 2/46*    (2006.01)
*A61F 2/30*    (2006.01)

(52) U.S. Cl.
CPC ............ *A61F 2/447* (2013.01); *A61F 2/4611* (2013.01); *A61F 2002/305* (2013.01);
(Continued)

(58) Field of Classification Search
CPC .... A61F 2002/3038; A61F 2002/30382; A61F 2002/30398; A61F 2002/304; A61F 2002/30401; A61F 2002/30484; A61F 2002/30485; A61F 2002/30576; A61F 2002/30579; A61F 2002/30594; A61F 2002/30596; A61F 2002/30598; A61F 2002/30777; A61F 2002/30787; A61F 2002/30782
See application file for complete search history.

(56) References Cited

U.S. PATENT DOCUMENTS

2010/0087925 A1   4/2010   Kostuik et al.
2010/0204739 A1   8/2010   Bae et al.
(Continued)

FOREIGN PATENT DOCUMENTS

CA    2853305    5/2013
CN    201244104    5/2009
(Continued)

OTHER PUBLICATIONS

Apparatus and Method for Fusing Opposing Spinal Vertebrae, Bramlet, Dale G. et al., U.S. Appl. No. 09/635,436, filed Aug. 11, 2000.
(Continued)

*Primary Examiner* — Samuel Hanna
(74) *Attorney, Agent, or Firm* — Lauff Law PLLC

(57) ABSTRACT

The present invention relates to a cage which is inserted between vertebral bodies of a cervical vertebra or spine during an operation for treating a cervical disc disease, myelosis, or fracture of the cervical vertebra or spine, and more particularly, to a cage with spikes, including upper and lower spikes which are attached to a clip inserted into a main body of the cage, unfolded upward and downward from the main body, and locked to vertebral bodies of a cervical vertebra or spine positioned at the top and bottom of the cage such that the cage is fixed and locked between the vertebral bodies.

8 Claims, 21 Drawing Sheets

(52) U.S. Cl.
CPC ............... *A61F 2002/30373* (2013.01); *A61F 2002/30472* (2013.01); *A61F 2002/30481* (2013.01); *A61F 2002/30484* (2013.01); *A61F 2002/30492* (2013.01); *A61F 2002/30504* (2013.01); *A61F 2002/30579* (2013.01); *A61F 2002/30629* (2013.01); *A61F 2002/30822* (2013.01); *A61F 2002/30892* (2013.01); *A61F 2002/30904* (2013.01); *A61F 2002/4475* (2013.01); *A61F 2310/00017* (2013.01); *A61F 2310/00023* (2013.01); *A61F 2310/00029* (2013.01); *A61F 2310/00089* (2013.01); *A61F 2310/00095* (2013.01); *A61F 2310/00131* (2013.01); *A61F 2310/00239* (2013.01)

(56) References Cited

U.S. PATENT DOCUMENTS

| | | | | |
|---|---|---|---|---|
| 2011/0230971 | A1* | 9/2011 | Donner | A61B 17/70 623/17.16 |
| 2012/0078373 | A1* | 3/2012 | Gamache | A61B 17/8625 623/17.16 |
| 2013/0110242 | A1* | 5/2013 | Kirwan | A61F 2/4465 623/17.16 |

FOREIGN PATENT DOCUMENTS

| | | |
|---|---|---|
| CN | 101878007 | 11/2010 |
| CN | 101917937 | 12/2010 |
| CN | 102458278 | 5/2012 |
| CN | 103251465 | 8/2013 |
| WO | WO0213732 | 2/2002 |
| WO | WO2010028045 | 3/2010 |
| WO | WO2010092893 | 8/2010 |
| WO | WO2012078657 | 6/2012 |
| WO | WO2012129206 | 9/2012 |
| WO | WO2013062716 | 5/2013 |

OTHER PUBLICATIONS

Intervertebral nucleus prosthesis and surgical procedure for implanting the same, Gau, Michel, U.S. Appl. No. 10/060,862, filed Jan. 30, 2002.
Intersomatic cage with unified grafts, Huppert, Jean, U.S. Appl. No. 10/276,712, filed Mar. 26, 2003.
Spinal Osteosynthesis Device and Preparation Method, Beaurain, Jacques et al., U.S. Appl. No. 10/473,999, filed Apr. 12, 2004.
Intervertebral Disc Prosthesis and Fitting Tools, Beaurain, Jacques et al., U.S. Appl. No. 10/476,565, filed Jun. 8, 2004.
Vertebral Cage Device With Modular Fixation, Louis, Christian et al., U.S. Appl. No. 10/483,563, filed May 21, 2004.
Progressive approach osteosynthesis device and preassembly method, Delecrin, Joel et al., U.S. Appl. No. 10/492,753, filed Aug. 9, 2004.
Plate for osteosynthesis device and method of preassembling such device, Delecrin, Joel et al., U.S. Appl. No. 10/492,827, filed Jul. 15, 2004.
Osseous anchoring device for a prosthesis, Huppert, Jean et al., U.S. Appl. No. 10/494,418, filed Jul. 22, 2004.
Implant for Osseous Anchoring with Polyaxial Head, Beaurain, Jacques et al., U.S. Appl. No. 10/498,234, filed Dec. 7, 2004.
Intervertebral Disc Prosthesis, Beaurain, Jacques et al., U.S. Appl. No. 10/533,846, filed Nov. 11, 2005.
Osseous anchoring implant with a polyaxial head and method for installing the implant, Renaud, Christian et al., U.S. Appl. No. 10/570,080, filed Jun. 9, 2006.
Device and method for sectioning a vertebral lamina, Mangione, Paolo, U.S. Appl. No. 10/575,065, filed May 30, 2006.
Intervertebral Disc Prosthesis, Hovorka, Istvan et al., U.S. Appl. No. 11/051,710, filed Feb. 4, 2005.
Intervertebral Disc Prosthesis, Zeegers, M. Willem, U.S. Appl. No. 11/098,266, filed Apr. 4, 2005.
Intervertebral Disc Prosthesis, Zeegers, Willem, U.S. Appl. No. 11/109,276, filed Apr. 18, 2005.
Instrumentation and Methods for Inserting an Intervertebral Disc Prosthesis, Dinville, Herve, U.S. Appl. No. 11/180,868, filed Jul. 13, 2005.
Intervertebral Disc Prosthesis, Rashbaum, Ralph et al., U.S. Appl. No. 11/341,007, filed Jan. 27, 2006.
Intervertebral Disc Prosthesis and Instrumentation for Insertion of the Prosthesis Between the Vertebrae, Rashbaum, Ralph et al., U.S. Appl. No. 11/362,253, filed Feb. 24, 2006.
Transforaminal intersomatic cage for an intervertebral fusion graft and an instrument for implanting the cage, Davis, Reginald James et al., U.S. Appl. No. 11/378,165, filed Mar. 17, 2006.
Intervertebral nucleus prosthesis and surgical procedure for implanting the same, Gau, Michel, U.S. Appl. No. 11/390,711, filed Mar. 27, 2006.
Intervertebral disc prosthesis insertion assemblies, Jodaitis, Alexandre et al., U.S. Appl. No. 11/676,237, filed Feb. 16, 2007.
Intersomatic cage with unified grafts, Huppert, Jean, U.S. Appl. No. 11/767,386, filed Jun. 22, 2007.
Nucleus Prostheses, Vila, Thierry et al., U.S. Appl. No. 11/874,144, filed Oct. 17, 2007.
Vertebral Support Device, Cho, Paul et al., U.S. Appl. No. 11/958,285, filed Dec. 17, 2007.
Intervertebral disc prosthesis, surgical methods, and fitting tools, Beaurain, Jacques et al., U.S. Appl. No. 12/025,677, filed Feb. 4, 2008.
Intersomatic cage, intervertebral prosthesis, anchoring device and implantation instruments, Allain, Jerome et al., U.S. Appl. No. 12/134,884, filed Jun. 6, 2008.
Transverse spinal linking device and system, Cho, Paul, U.S. Appl. No. 12/172,074, filed Jul. 11, 2008.
Transforaminal intersomatic cage for an intervertebral fusion graft and an instrument for implanting the cage, Davis, Reginald James et al., U.S. Appl. No. 12/279,664, filed Apr. 22, 2009.
Intervertebral Disc Prosthesis, Zeegers, Willem, U.S. Appl. No. 12/360,050, filed Jan. 26, 2009.
Intervertebral Disc Prosthesis, Zeegers, M. Willem, U.S. Appl. No. 12/391,086, filed Feb. 23, 2009.
Spinal Osteosynthesis Device and Preparation Method, Beaurain, Jacques et al., U.S. Appl. No. 12/409,327, filed Mar. 23, 2009.
Intervertebral disc prosthesis, Beaurain, Jacques et al., U.S. Appl. No. 12/424,364, filed Apr. 15, 2009.
Vertebral Cage Device With Modular Fixation, Louis, Christian et al., U.S. Appl. No. 12/430,768, filed Apr. 27, 2009.
Instrumentation and Methods for Inserting an Intervertebral Disc Prosthesis, Dinville, Herve, U.S. Appl. No. 12/435,955, filed May 5, 2009.
Intervertebral disc prosthesis insertion assemblies, Jodaitis, Alexandre et al., U.S. Appl. No. 12/527,373, filed Mar. 19, 2010.
Intervertebral implant having extendable bone fixation members, Brett, Darrell C., U.S. Appl. No. 12/884,664, filed Sep. 17, 2010.
Intervertebral Disc Prosthesis, Rashbaum, Ralph et al., U.S. Appl. No. 12/955,898, filed Nov. 29, 2010.
Instruments and Methods for Removing Fixation Devices from Intervertebral Implants, Dinville, Herve et al., U.S. Appl. No. 13/158,761, filed Jun. 13, 2011.
Intervertebral Disc Prosthesis, Zeegers, M. Willem, U.S. Appl. No. 13/215,123, filed Aug. 22, 2011.
Interspinous Implant and Implantation Instrument, Dinville, Hervé et al., U.S. Appl. No. 13/369,650, filed Feb. 9, 2012.
Vertebral Cage Device With Modular Fixation, Louis, Christian et al., U.S. Appl. No. 13/438,352, filed Apr. 3, 2012.
Plate for osteosynthesis device and method of preassembling such device, Delecrin, Joel et al., U.S. Appl. No. 13/454,927, filed Apr. 24, 2012.
Anchoring Device and System for an Intervertebral Implant, Intervertebral Implant and Implantation Instrument, Dinville, Hervé et al., U.S. Appl. No. 13/520,041, filed Nov. 26, 2012.

(56) References Cited

OTHER PUBLICATIONS

Anchoring Device and System for an Intervertebral Implant, Intervertebral Implant and Implantation Instrument, Dinville, Hervé et al., U.S. Appl. No. 13/538,078, filed Jun. 29, 2012.
Transforaminal intersomatic cage for an intervertebral fusion graft and an instrument for implanting the cage, Davis, Reginald James et al., U.S. Appl. No. 13/585,063, filed Aug. 14, 2012.
Intervertebral Disc Prosthesis, Zeegers, Willem, U.S. Appl. No. 13/603,043, filed Sep. 4, 2012.
Intervertebral Disc Prosthesis, Beaurain, Jacques et al., U.S. Appl. No. 13/616,448, filed Sep. 14, 2012.
Intervertebral Disc Prosthesis and Instrumentation for Insertion of the Prosthesis Between the Vertebrae, Rashbaum, Ralph et al., U.S. Appl. No. 13/620,797, filed Sep. 15, 2012.
Intersomatic cage, intervertebral prosthesis, anchoring device and implantation instruments, Allain, Jerome et al., U.S. Appl. No. 13/732,244, filed Dec. 31, 2012.
Anchoring device and system for an intervertebral implant, intervertebral implant and implantation instrument, Chataigner, Hervé et al., U.S. Appl. No. 13/774,547, filed Feb. 22, 2013.
Transforaminal intersomatic cage for an intervertebral fusion graft and an instrument for implanting the cage, Davis, Reginald James et al., U.S. Appl. No. 13/854,808, filed Apr. 1, 2013.
Spinal Osteosynthesis Device and Preparation Method, Beaurain, Jacques et al., U.S. Appl. No. 13/873,190, filed Apr. 29, 2013.
Instrumentation and Methods for Inserting an Intervertebral Disc Prosthesis, Dinville, Herve, U.S. Appl. No. 13/892,933, filed May 13, 2013.
Intervertebral Disc Prosthesis Insertion Assemblies, Jodaitis, Alexandre et al., U.S. Appl. No. 13/919,704, filed Jun. 17, 2013.
Intervertebral implant having extendable bone fixation members, Brett, Darrell C., U.S. Appl. No. 14/064,434, filed Oct. 28, 2013.
Interspinous Implant and Instrument for Implanting an Interspinous Implant, Dinville, Hervé et al., U.S. Appl. No. 14/130,286, filed Jul. 3, 2014.
Intersomatic cage with unified grafts, Huppert, Jean, U.S. Appl. No. 14/149,357, filed Jan. 7, 2014.
Nucleus Prosthesis, Vila, Thierry et al., U.S. Appl. No. 14/159,161, filed Jan. 20, 2014.
Interveterbral disc prosthesis insertion assemblies, Jodaitis, Alexandre et al., U.S. Appl. No. 14/242,177, filed Apr. 1, 2014.
Vertebral implant, vertebral fastening device of the implant and implant instrumentation, Dinville, Hervé et al., U.S. Appl. No. 14/246,442, filed Apr. 7, 2014.
Interspinous Implant and Instrument for Implanting an Interspinous Implant, Dinville, Hervé et al., U.S. Appl. No. 14/252,754, filed Apr. 14, 2014.
Anchoring device for a spinal implant, spinal implant and implantation instrumentation, Chataigner, Hervé et al., U.S. Appl. No. 14/252,852, filed Apr. 15, 2014.
Intervertebral Disc Prosthesis, Beaurain, Jacques et al., U.S. Appl. No. 14/306,785, filed Jun. 17, 2014.
Intervertebral Disc Prosthesis and Instrumentation for Insertion of the Prosthesis Between the Vertebrae, Steib, Jean-Paul, U.S. Appl. No. 14/325,317, filed Jul. 7, 2014.
Anchoring device and system for an intervertebral implant, intervertebral implant and implantation instrument, Chataigner, Hervé et al., U.S. Appl. No. 14/380,714, filed Aug. 23, 2014.
Cage Having Spike, Kim, Seo-Kon et al., U.S. Appl. No. 14/460,536, filed Aug. 15, 2014.
Osseous anchoring implant with a polyaxial head and method for installing the implant, Renaud, Christian et al., U.S. Appl. No. 14/497,321, filed Sep. 26, 2014.
Intervertebral Disc Prosthesis, Hovorka, Istvan et al., U.S. Appl. No. 14/513,818, filed Oct. 14, 2014.
Plate for osteosynthesis device and preassembly method, Delecrin, Joel et al., U.S. Appl. No. 14/584,674, filed Dec. 29, 2014.
Intervertebral Implant Having Extendable Bone Fixation Members, Brett, Darrell C., U.S. Appl. No. 14/594,770, filed Jan. 12, 2015.
Vertebral implant, device for vertebral attachment of the implant and instrumentation for implantation thereof, Ameil, Marc et al., U.S. Appl. No. 14/638,746, filed Mar. 4, 2015.
Intervertebral Disc Prosthesis, Zeegers, Willem, U.S. Appl. No. 14/642,696, filed Mar. 9, 2015.
Vertebral Support Device, Cho, Paul et al., U.S. Appl. No. 14/642,752, filed Mar. 10, 2015.
Intervertebral Disc Prosthesis, Rashbaum, Ralph et al., U.S. Appl. No. 14/659,587, filed Mar. 16, 2015.
Anchoring device and system for an intervertebral implant, intervertebral implant and implantation instrument, Chataigner, Hervé et al., U.S. Appl. No. 14/721,818, filed May 26, 2015.
Intervertebral Disc Prosthesis, Zeegers, Willem, U.S. Appl. No. 14/726,557, filed May 31, 2015.
Anchoring Device and System for an Intervertebral Implant, Intervertebral Implant and Implantation Instrument, Dinville, Hervé et al., U.S. Appl. No. 14/726,558, filed May 31, 2015.
Vertebral Cage Device With Modular Fixation, Louis, Christian et al., U.S. Appl. No. 14/798,900, filed Jul. 14, 2015.
Bone Implants, Lavigne, Christophe et al., U.S. Appl. No. 14/815,900, filed Jul. 31, 2015.
Devices, Methods, and Systems to Implant and Secure a Fusion Cage or Intervertebral Prosthesis for Spinal Treatment, Stewart, Will et al., U.S. Appl. No. 14/827,297, filed Aug. 15, 2015.
Vertebral implant, vertebral fastening device of the implant and implant instrumentation, Dinville, Herve et al., U.S. Appl. No. 14/891,322, filed Nov. 13, 2015.
Instruments and Methods for Removing Fixation Devices from Intervertebral Implants, Dinville, Herve et al., U.S. Appl. No. 14/931,007, filed Nov. 3, 2015.
Instrumentation and Methods for Inserting an Intervertebral Disc Prosthesis, Dinville, Herve, U.S. Appl. No. 15/012,815, filed Feb. 1, 2016.
Intervertebral Disc Prosthesis, Beaurain, Jacques et al., U.S. Appl. No. 15/049,934, filed Feb. 22, 2016.
Intervertebral Disc Prosthesis and Instrumentation for Insertion of the Prosthesis Between the Vertebrae, Steib, Jean-Paul, U.S. Appl. No. 15/049,995, filed Feb. 22, 2016.
Anchoring device for a spinal implant, spinal implant and implantation instrumentation, Chataigner, Hervé et al., U.S. Appl. No. 15/115,659, filed Jul. 29, 2016.
Interspinous Implant and Implantation Instrument, Dinville, Hervé et al., U.S. Appl. No. 15/145,413, filed May 3, 2016.
Implant for Osseous Anchoring with Polyaxial Head, Beaurain, Jacques et al., U.S. Appl. No. 15/145,431, filed May 3, 2016.
Intervertebral disc prosthesis, surgical methods, and fitting tools, Beaurain, Jacques et al., U.S. Appl. No. 15/150,316, filed May 9, 2016.
Interspinous Implant and Instrument for Implanting an Interspinous Implant, Dinville, Hervé et al., U.S. Appl. No. 15/225,612, filed Aug. 1, 2016.
Intervertebral Disc Prosthesis, Zeegers, M. Willem, U.S. Appl. No. 15/269,923, filed Sep. 19, 2016.
Intervertebral Implant Having Extendable Bone Fixation Members, Brett, Darrell C., U.S. Appl. No. 15/289,861, filed Oct. 10, 2016.
Vertebral implant, device for vertebral attachment of the implant and instrumentation for implantation thereof, Ameil, Marc et al., U.S. Appl. No. 15/309,197, filed Nov. 6, 2016.
Intervertebral Disc Prosthesis Insertion Assemblies, Jodaitis, Alexandre et al., U.S. Appl. No. 15/340,565, filed Nov. 1, 2016.
Nucleus Prosthesis, Vila, Thierry et al., U.S. Appl. No. 15/391,305, filed Dec. 27, 2016.
Plate for osteosynthesis device and preassembly method, Delecrin, Joel et al., U.S. Appl. No. 15/414,523, filed Jan. 24, 2017.
Implant for Osseous Anchoring with Polyaxial Head, Beaurain, Jacques et al., U.S. Appl. No. 15/426,938, filed Feb. 7, 2017.
Intervertebral Disc Prosthesis, Zeegers, Willem, U.S. Appl. No. 15/432,795, filed Feb. 14, 2017.
System of spinal arthodesis implants, Mercier, Alexis et al., U.S. Appl. No. 15/442,591, filed Feb. 24, 2017.
Intervertebral Disc Prosthesis, Rashbaum, Ralph et al., U.S. Appl. No. 15/464,639, filed Mar. 21, 2017.

(56) References Cited

OTHER PUBLICATIONS

Transforaminal intersomatic cage for an intervertebral fusion graft and an instrument for implanting the cage, Davis, Reginald James et al., U.S. Appl. No. 15/465,143, filed Mar. 21, 2017.
Bone Implants, Lavigne, Christophe et al., U.S. Appl. No. 15/501,166, TBD.
Bone anchoring system, associated implant and instrumentation, Lequette, Samuel et al., U.S. Appl. No. 15/582,568, filed Apr. 28, 2017.
Intervertebral Fusion Cage with Retractable-Extrudable Pins, Brett, Darrell C., U.S. Appl. No. 61/243,297, filed Sep. 17, 2009.
Intervertebral Fusion Cage with Retractable-Extrudable Pins, Brett, Darrell C., U.S. Appl. No. 61/260,364, filed Nov. 11, 2009.
Korean Patent Office; Office Action; dated Feb. 16, 2015; Korean Patent Office; Seoul, South Korea.
Solco Biomedical; Amendment; dated Apr. 16, 2015; Korean Patent Office; Seoul, South Korea.
Solco Biomedical; Reply; dated Apr. 16, 2015; Korean Patent Office; Seoul, South Korea.
Japanese Patent Office; dated Office Action; May 11, 2015; Japanese Patent Office; Tokyo, Japan.
Chinese Patent Office; dated Office Action; Dec. 8, 2015; Chinese Patent Office; Bejing, China.

* cited by examiner

CAGE HAVING SPIKE

CROSS-REFERENCE TO RELATED APPLICATIONS

This application claims the benefit of Korean Patent Application No. 10-2013-108840, filed on Sep. 11, 2013 in the Korean Intellectual Property Office, which is incorporated herein by reference in its entirety.

BACKGROUND OF THE INVENTION

1. Field of the Invention

The present invention relates to a cage which is inserted between vertebral bodies of a cervical vertebra or spine during an operation for treating a cervical disc disease, myelosis, or fracture of the cervical vertebra or spine, and more particularly, to a cage including upper and lower spikes which are attached to a clip inserted into a main body of the cage, unfolded to protrude from the top and bottom of the main body, and locked to vertebral bodies of a cervical vertebra or spine positioned at the top and bottom of the cage such that the cage is fixed between the vertebral bodies.

2. Description of Related Art

In general, an operation of inserting an artificial compensation-chain cage between vertebral bodies of a cervical vertebra or spine is performed in order to treat a cervical disc disease, myelosis, or fracture of a cervical vertebra or spine in the orthopedics department or neurosurgery department. More specifically, an operator removes a cervical disc of a diseased part so as to eliminate compression of nerve, and inserts the artificial compensation-cage to recover and maintain the interval of the part from which the cervical disc has been removed.

Such a cage is likely to be moved within the intervertebral space by stress applied when the patient moves. Thus, an additional unit must be provided to prevent the pivot of the cage while preventing the movement of the cervical vertebra or spine within the intervertebral space.

According to Korean Patent Laid-open Publication No. 10-2011-33707 which has disclosed a cervical vertebral body fusion device, Korean Patent No. 900991 which has disclosed a cage for spinal implant, and Korean Patent Laid-open Publication No. 10-2011-11049 which has disclosed a fusion cage between vertebral bodies, a cage is inserted into a part from which an intervertebral disc has been removed, and a reinforcement plate having a predetermined length is fixed to a cervical vertebra or spine through a screw, thereby preventing the displacement of the inserted cage.

In the above-described techniques, however, the reinforcement plate is fixed at the front of the cage through the screw. Thus, the head of the screw inserted into the plate or a part of the plate may protrude more than protruding parts of the cervical vertebra or spine, which are positioned at the top and bottom of the part from which the intervertebral disk has been removed and in which the cage is installed. In this case, according to a force applied when a patient moves with time, the cage may be moved or pivoted within the intervertebral space such that the protruding head of the screw within the intervertebral space comes in contact with blood tissues or nerve tissues passing through the cervical vertebra or spine. Thus, there is a demand for the development of a more stable cage.

Furthermore, the plate and the screw are used to fix the cage. In this case, it is extremely difficult to fix the plate through the screw in such a small intervertebral space, while much attention is needed. Thus, special technical skills are required for an operator.

SUMMARY OF THE INVENTION

Accordingly, the present invention has been made to solve the above-mentioned problems involved in the prior art, and it is an object of the present invention to provide a cage with spikes which is capable of preventing the occurrence of a protruding part of a screw so as to minimize interference with blood tissues or nerve tissues passing through the cervical vertebra or spine when the cage is placed, and performing a procedure for fixing the cage in a relatively easy and simple manner, thereby improving the stability of operation.

To accomplish the above object, the present invention provides a cage with spikes which includes upper and lower spikes which are attached to a clip inserted into a main body of the cage, unfolded upward and downward from the main body, and locked to vertebral bodies of a cervical vertebra or spine positioned at the top and bottom of the cage such that the cage is fixed and locked between the vertebral bodies.

The cage in accordance with the embodiment of the present invention has the following effects.

First, the cage is locked and fixed between the vertebral bodies of a cervical vertebra or spine at the part from which an intervertebral disk has been removed, by the spikes unfolded upward and downward from the main body of the cage. Thus, it is possible to significantly reduce the possibility that the screw for fixing the cage or a part of the plate will interfere with the nerve tissue or blood tissue passing through the cervical vertebra or spine at the part from which the intervertebral disk was removed and in which the cage is installed. Furthermore, prognosis of a patient having received an intervertebral disk surgery may be improved.

Furthermore, the cage in accordance with the embodiment of the present does not employ a plate or screw unlike the conventional cages, but includes the spikes. Thus, it is possible to omit a complicated operation of fixing a plate through a screw in a small intervertebral space in the related art. Therefore, the convenience of the procedure may be improved, and the operation process may be simplified to provide the stability of the operation.

BRIEF DESCRIPTION OF THE DRAWINGS

The above and other objects, features and advantages of the present invention will be apparent from the following detailed description of the preferred exemplary embodiments of the invention in conjunction with the accompanying drawings, in which.

EXPLANATION ON SYMBOLS

Figure 1:
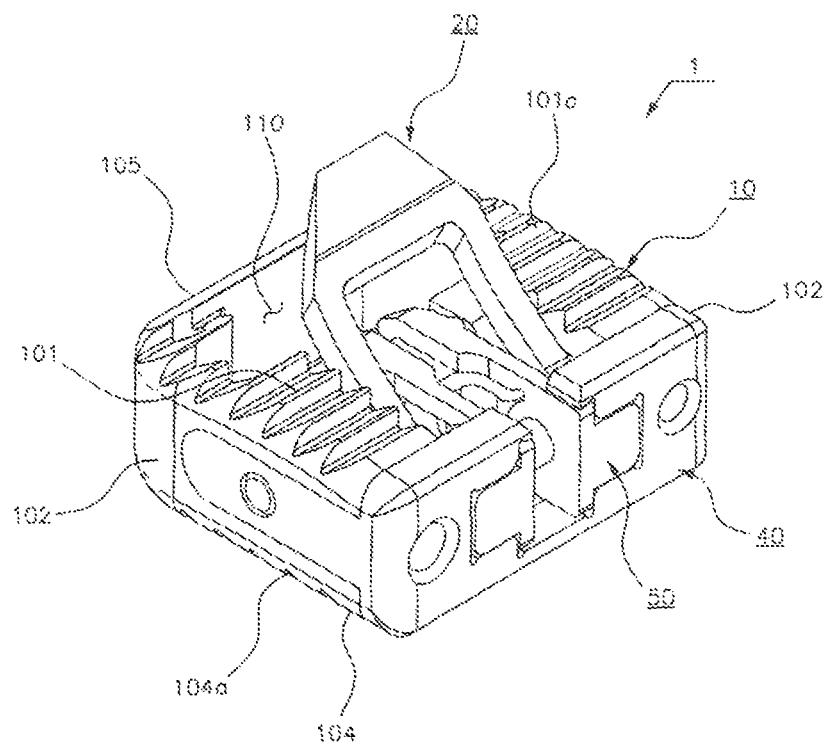
FIG. 1 is a perspective view of a cage in accordance with an embodiment of the present invention.

1: cage 10: main body 101: top surface 02: side surface 103: front surface 104: bottom surface 105: rear surface 110: bone fusion hole 101a,104a: saw-toothed bodies 120: insertion hole 130: channel part 140: inclined part 141; upper inclined surface 142; top plane surface 143; lower inclined surface 144; bottom plane surface 145; inner wall surfaces 146; protruding surface 151; mounting grooves 152; upper wall 153; lower wall 154: side wall 20: upper spike 21: upper blade 22,23: arms 24,25: fastening holes 30: lower spike 31: lower blade 32, 33: arms 34, 35: fastening holes 40: guide block 41: front plate 42: left bar 43: right bar 44: through-hole 45: entrance hole 46: insertion hole 50: clip 51: right retaining jaw 52: left retaining jaw 53: right rib 54: left rib 55: lower rib 56: through-hole 57: base 60: guide block coupling pin 61: clip coupling pin 45 200: insertion mechanism 210: head 211: left head 212: right head 213: upper head 220: first lower support rod 221: push stick guide 230: second lower support rod 240: push stick 241: push plate 242: rod body 243: boss 244: coupling member 250: upper support rod 251: upper support rod guide 252: support body D1: upper vertebral body D2: lower vertebral body

DESCRIPTION OF THE PREFERRED EMBODIMENTS

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

The drawings are provided as examples for communicating the idea of the present invention to those skilled in the art. Thus, the present invention is not limited to the drawings, but may be embodied into other forms.

Furthermore, as long as terms used in this specification are not defined differently, the terms have meanings which are typically understood by those skilled in the art to which the present invention pertains. Moreover, detailed descriptions related to well-known functions or configurations will be ruled out in order not to unnecessarily obscure subject matters of the present invention.

Figure 2:
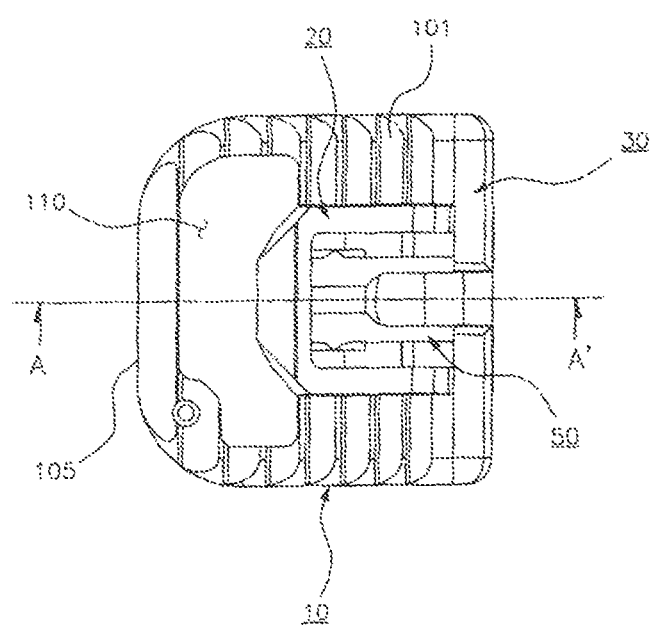
FIG. 2 is a plan view of the cage in accordance with the embodiment of the present invention.
Figure 3:
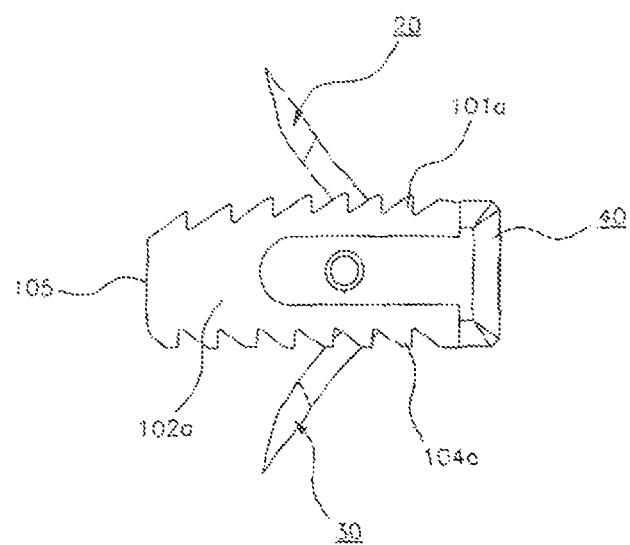
FIG. 3 is a cross-sectional view taken along line A-A' of FIG. 2.

FIG. 1 is a perspective view of a cage in accordance with an embodiment of the present invention. FIG. 2 is a plan view of the cage in accordance with the embodiment of the present invention. FIG. 3 is a cross-sectional view taken along line A-A' of FIG. 2.

Referring to FIGS. 1 to 3, the cage 1 in accordance with the embodiment of the present invention includes a main body 10, a clip 50, upper and lower spikes 20 and 30, and a guide block 40. The clip 50 is inserted into the main body 10. The upper and lower spikes 20 and 30 are coupled to the clip 50 and unfolded to protrude upward and downward through the insertion of the clip 50. The guide block 40 is coupled to the main body 10 so as to guide the insertion of the clip 50.

The upper and lower spikes 20 and 30 unfolded upward and downward from the main body 10 are locked to upper and lower vertebral bodies of a cervical vertebral or spine positioned at the top and bottom of the cage 1 such that the cage 1 is fixed and locked between the vertebral bodies of the cervical vertebral or spine.

The main body 10 of the cage 1 has a hexahedral shape including a top surface 101, both side surfaces 102, a front surface 103, a bottom surface 104, and a rear surface 105. The corners of the main body 10 are rounded.

As illustrated in FIG. 2, the main body 10 has a bone fusion hole 110 formed through the top and bottom surfaces 101 and 104 and a channel part 130 formed therein. The channel part 130 corresponds to a space having an opening through which the clip 50 is inserted into the main body 10 of the cage 1 from the front surface 103.

Furthermore, the main body 10 has an inclined part 140 formed therein. The inclined part 140 guides movement of the upper and lower spikes 20 and 30, when the upper and lower spikes 20 and 30 coupled to the clip 50 inserted through the channel part 130 are unfolded upward and downward. The top of the inclined part 140 is opened so as to unfold the upper and lower spikes 20 and 30 to the outside of the main body 10. The inclined part 140 will be described in more detail.

As illustrated in FIG. 3, the main body 10 has saw-toothed bodies 101a and 104a formed on the top and bottom surfaces 101 and 104 thereof. When the cage 1 is inserted between vertebral bodies of a cervical vertebral or spine, the saw-toothed bodies 10a and 104a improve the contact between the upper and lower vertebral bodies.

Figure 4:
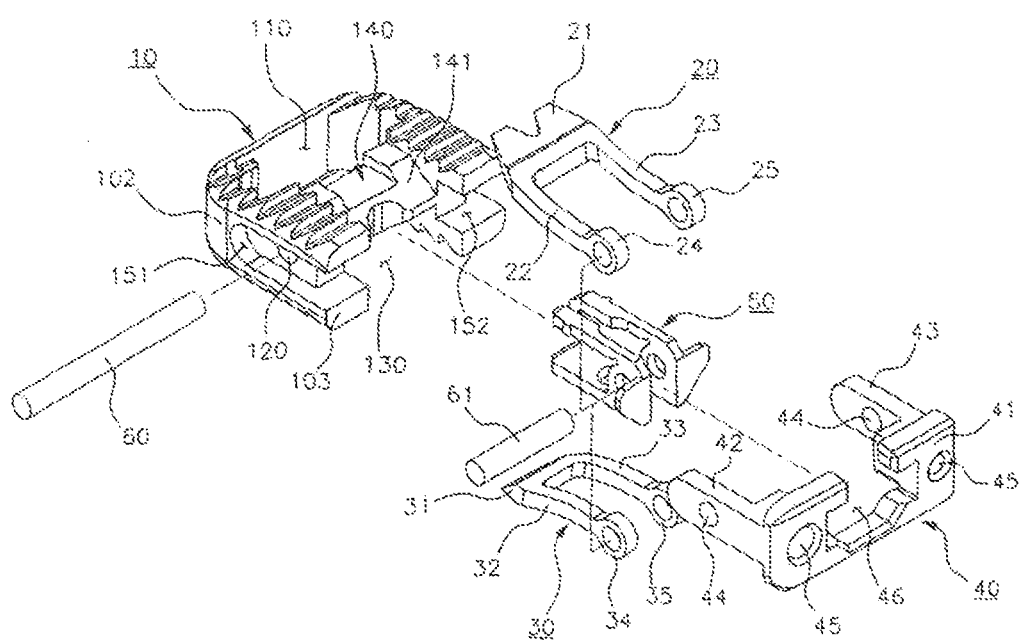
FIG. 4 is an exploded perspective view of the cage in accordance with the embodiment of the present invention.

FIG. 4 is an exploded perspective view of the cage in accordance with the embodiment of the present invention.

As illustrated in FIG. 4, the guide block 40 is coupled to the front surface 103 of the main body 10.

The guide block 40 includes left and right bars 42 and 43 which are formed in the left and right sides thereof and inserted into mounting grooves 151 formed in the left and right side surfaces 102 of the main body 10, respectively, and a guide block coupling pin 61 is passed through through-holes 44 which are formed in the left and right bars 42 and 43 of the guide block 40 and an insertion hole 120 which is vertically formed through the right side surface 102 from the left side surface 102 of the main body 10. Thus, the main body 10 and the guide block 40 are coupled to each other.

After the main body 10 and the guide block 40 are coupled, the clip 50 coupled to the upper and lower spikes 20 and 30 is inserted into the main body 10 through an entrance hole 46 of the guide block 40.

Then, the upper and lower spikes 20 and 30 coupled to the clip 50 are guided along the upper and lower inclined surfaces 141 and 143 of the inclined part 140 formed in the main body 10, and unfolded to protrude upward and downward from the main body 10 while moving upward and downward.

At this time, the upper and lower spikes 20 and 30 are coupled to the clip 50 through the clip coupling pin 60.

Hereafter, the respective elements of the cage 1 in accordance with the embodiment of the present invention will be described in detail.

Figure 5A:
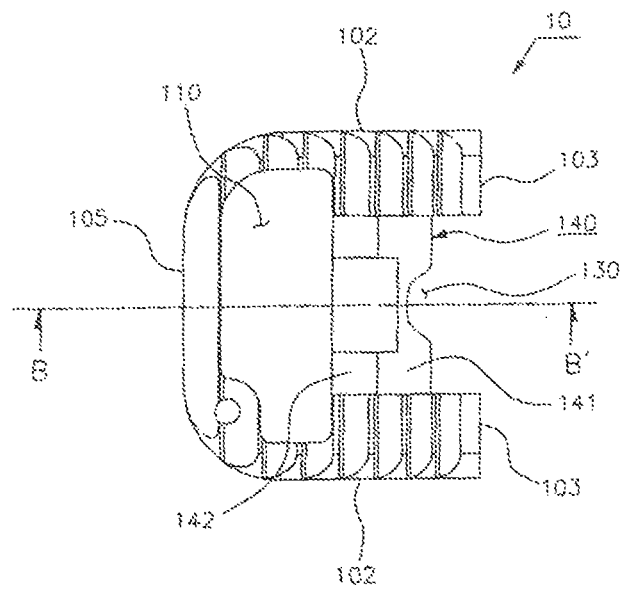
FIGS. 5A to 5D are detailed diagrams of a main body of the cage in accordance with the embodiment of the present invention, FIG. 5C being a cross-sectional view taken along the line B-B' of FIG. 5A.
Figure 5B:
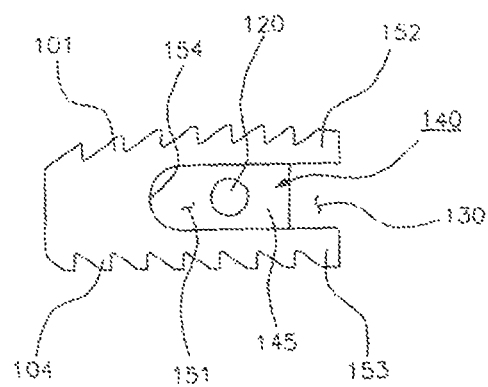
Figure 5C:
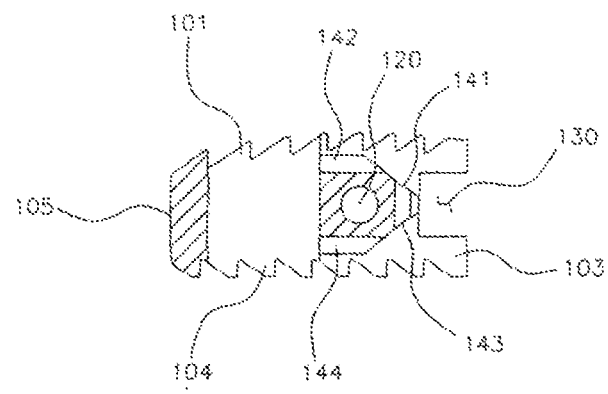
Figure 5D:
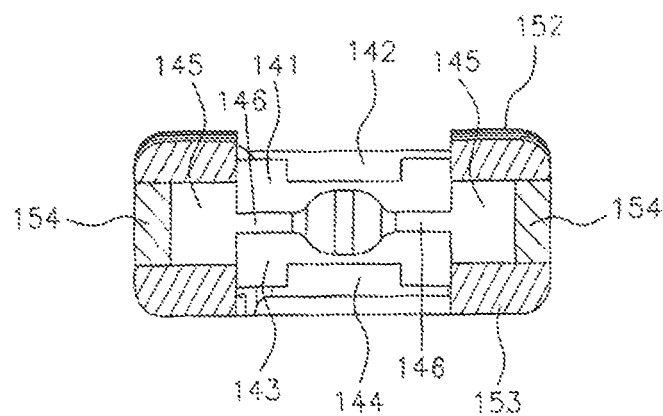

FIGS. 5A to 5D are detailed diagram of the main body of the cage in accordance with the embodiment of the present invention. FIG. 5A is a plan view, FIG. 5B is a side view, FIG. 5C is a cross-sectional view taken along line B-B' of FIG. 5A, and FIG. 5D is a front view.

As described above, the main body 10 of the cage 1 is formed in a hexahedral shape having the top surface 101, both side surfaces 102, the front surface 103, the bottom surface 104, and the rear surface 105, the bone fusion hole 110 is formed through the top and bottom surfaces 101 and 104, and the channel part 130 provides a space such that the clip 50 is inserted from the front surface 103 of the main body 10 and fixed to the central part of the main body 10.

When the upper and lower spikes 20 and 30 coupled to the clip 50 inserted through the channel part 130 are unfolded upward and downward, the inclined part 140 formed in the main body 10 guides the movement of the upper and lower spikes 20 and 30. The top and bottom of the inclined part 140 are opened to unfold the upper and lower spikes 20 and 30 to the outside of the main body 10.

The inclined part 140 has an upper inclined surface 141 formed to guide the upward movement of the upper spike 20, and a top plane surface 142 is formed at an end of the upper inclined surface 141.

Furthermore, the inclined part 140 has a lower inclined surface 143 formed to guide the downward movement of the lower spike 30, and a bottom plane surface 142 is formed at an end of the lower inclined surface 143.

Furthermore, a protruding surface 146 with a predetermined width is formed at the connection between the upper and lower inclined surfaces 141 and 142 of the inclined part 140, and an inner wall surface of a base 57 of the clip 50 is locked to the protruding surface 146 so as to stop the insertion of the clip 50 into the channel part 130.

The inclined part 140 has inner wall surfaces 145 formed at the left and right side surfaces so as to be stepped with respect to the top and bottom surfaces 101 and 104 of the main body 10.

The mounting grooves 151 are formed outside the respective inner wall surfaces 145 such that the left and right bars 42 and 43 of the guide block 40 are mounted in the mounting grooves 151. The mounting groove 151 corresponds to a space formed at the side surface 102 of the main body 10 and includes an upper wall 152, a lower wall 153, and a side wall 154.

The main body 10 of the cage 1 in accordance with the embodiment of the present invention is formed of a metal oz metal alloy such as titanium, zirconium, zirconium oxide, hafnium, platinum, rhodium, niobium, stainless steel for surgery, cobalt chrome (CoCr)-steel, or tantalum or a polymer material such as fiber-reinforced plastic or polyether ether ketone (PEEK). Furthermore, a metal such as aluminum, medical steel, or gold may be added to the metal alloy.

Desirably, PEEK having excellent mechinability and durability may be used as the material of the main body 10.

The bone fuse hole 110 formed in the body 10 may be filled with bone chips extracted from a patient's ilium, for an operation of placing the cage 1. The bone chips stored in the bone fusion hole 110 may grow through the cage as the time passes after the operation, thereby fusing the intervertebral disk of the diseased part to the cervical vertebra or spine.

The insertion hole 120 is formed through the left and right surfaces 102 of the main body 10, in order to fasten the guide block coupling pin 60 for coupling the guide block 40 to the main body 10.

Figure 6A:
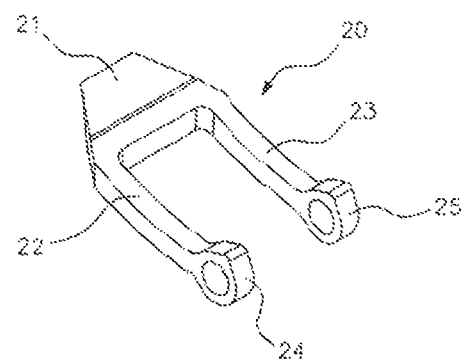
FIGS. 6A to 6C are detailed diagrams of an upper spike of the cage in accordance with the embodiment of the present invention, FIG. 6C being a cross-sectional view taken along the line C-C' of FIG. 6B.
Figure 6B:
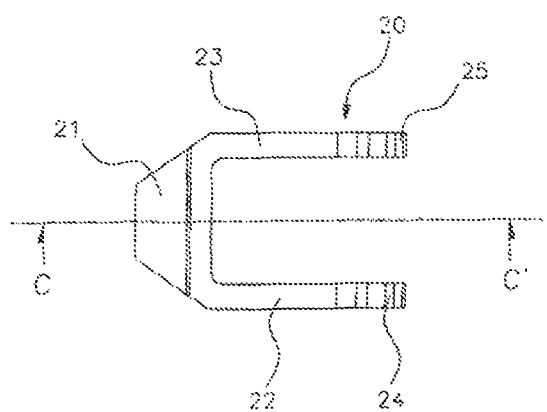
Figure 6C:
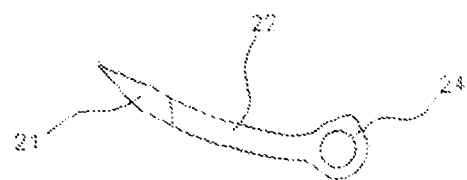
Figure 7A:
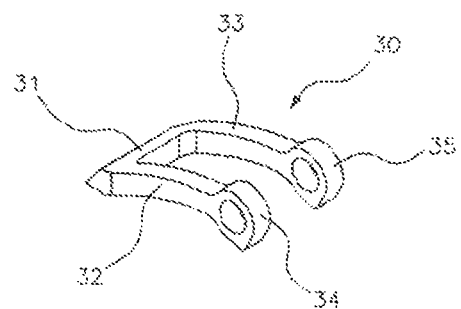
FIGS. 7A to 7C are detailed diagrams of a lower spike of the cage in accordance with the embodiment of the present invention, FIG. 7C being a cross-sectional view taken along the line D-D' of FIG. 5B.
Figure 7B:
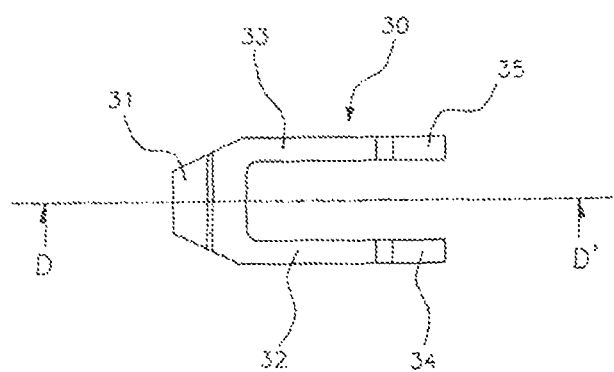
Figure 7C:
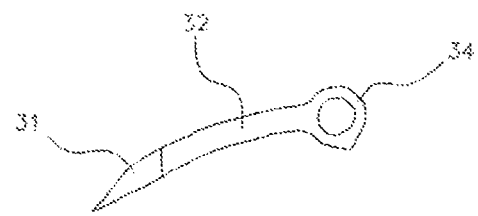
Figure 8A:
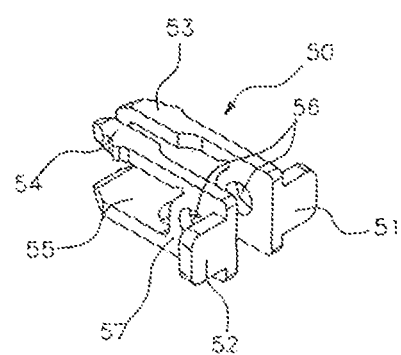
FIGS. 8A to 8D are detailed diagrams of a clip of the cage in accordance with the embodiment of the present invention, FIG. 8C being a cross-sectional view taken along the line E-E' of FIG. B.
Figure 8B:
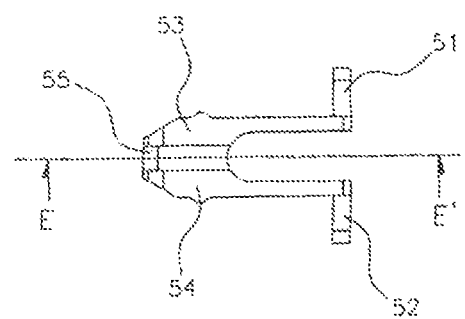
Figure 8C:
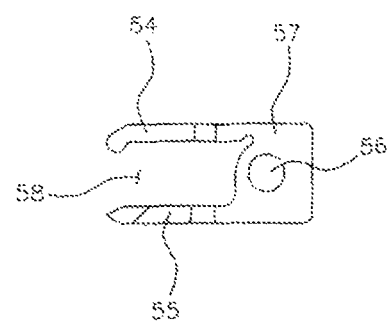
Figure 8D:
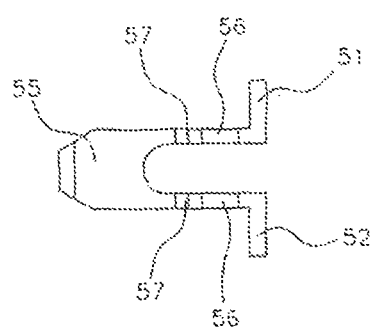

FIGS. 6A to 6C are detailed diagrams of the upper spike of the cage in accordance with the embodiment of the present invention. FIGS. 7A to 7C are detailed diagrams of the lower spike of the cage in accordance with the embodiment of the present invention. FIGS. 8A to 8D are detailed diagrams of the clip of the cage in accordance with the embodiment of the present invention.

Referring to FIG. 6A to 6C, the upper spike 20 coupled to the clip 50 of the cage 1 includes an upper blade 21, arms 22 and 23, and fastening holes 24 and 25. The blade 21 has a pointed end surface formed at an end thereof. The arms 22 and 23 are formed at both sides of the upper blade 21 so as to be extended and inclined downward. The fastening holes 24 and 25 are formed at ends of the respective arms 22 and 23 such that the clip coupling pin 61 for coupling the clip 50 is inserted into the fastening holes 24 and 25.

The upper spike 20 has such a structure that is inclined upward at an increasing angle from the fastening holes 24 and 25. Thus, when the cage 1 in accordance with the embodiment of the present invention is inserted between upper and lower vertebral bodies of a cervical vertebra or spine, the pointed end surface of the upper blade 21 formed at an increasing angle is put into the upper vertebral body and locked to the upper vertebral body such that the cage 1 may be reliably inserted.

Referring to FIGS. 7A to 7C, the lower spike 30 coupled to the clip 50 of the cage 1 includes a lower blade 31, arms 32 and 33, and fastening holes 34 and 35, like the upper spike 20. The lower blade 31 is formed at an end of the lower spike 30 and has a pointed end surface. The arms 32 and 33 are formed at both sides of the lower blade 31 so as to be inclined and extended upward. The fastening holes 34 and 35 are formed at ends of the respective arms 32 and 33 such that a clip coupling pin 61 for coupling the clip 50 is inserted into the fastening holes 34 and 35.

The lower spike 30 has such a structure that is inclined downward at a decreasing angle from the fastening holes 34 and 35. Thus, when the cage 1 in accordance with the embodiment of the present invention is inserted between the upper and lower vertebral bodies of the cervical vertebra or spine, the pointed end surface of the lower blade 31 formed at a decreasing angle is put into the lower vertebral body and locked to the lower vertebral body such that the cage 1 may be reliably inserted with the upper spike 20.

Referring to FIGS. 8a to 8d, the clip 50 for coupling the upper and lower spikes 20 and 30 of the cage 1 includes right and left retaining jaws 51 and 52 and right and left ribs 53 and 54. The right and left retaining jaws 51 and 52 having a plate shape are formed at the front of the base 57 so as to be contacted with an insertion mechanism 200 which serves to push the clip 50 to the inside of the main body 10, and the right and left ribs 53 and 54 are formed at the top rear of the base 57 and extended to be slid and mounted on the top plane surface 142 of the inclined part 140 of the main body 10, when the clip 50 is inserted into the main body 10.

The clip 50 further includes a lower rib 55 formed at the bottom rear thereof and extended to be slid and mounted on the bottom plane surface 144 of the inclined part 140 of the main body 10, when the clip 50 is inserted into the main body 10.

The clip 50 further includes a through-hole 56 formed through the base 57 of the clip 50 so as to fasten the clip coupling pin 61 for coupling the upper and lower spikes 20 and 30.

FIGS. 9 and 10 are diagrams illustrating a state in which the upper and lower spikes of the cage in accordance with the embodiment of the present invention are coupled to the clip.

Figure 9A:
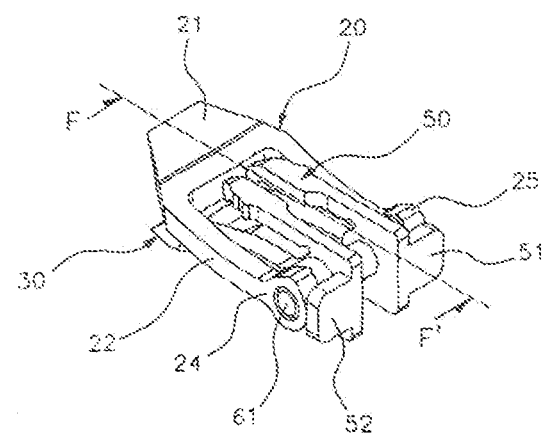
FIG. 9A is a perspective illustrating a state in which upper and lower spikes of the cage, in accordance with the embodiment of the present invention, are coupled to the clip.
Figure 9B:
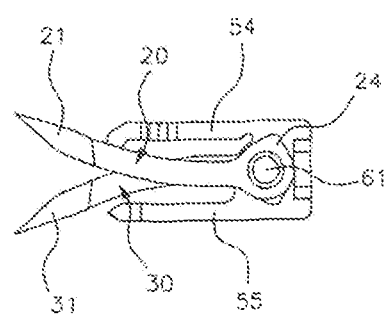
FIG. 9B is a cross-sectional view taken along the line F-F' in FIG. A.

Referring to FIGS. 9A and 9B, the lower spike 30 is positioned inside both arms 22 and 23 of the upper spike 20, and the fastening holes 24 and 25 of the upper spike 20 and the fastening holes 34 and 35 of the lower spike 30 are aligned with each other. In such a state, the fastening holes 24, 25, 34, and 35 of the respective spikes are aligned with the through-holes 56 formed in the base 57 of the clip 50, and the clip coupling pin 61 is then passed through the fastening holes 24, 25, 34, and 35 and the through-holes 56 of the clip 50 so as to couple the upper and lower spikes 20 and 30 to the clip 50.

Figure 10A:
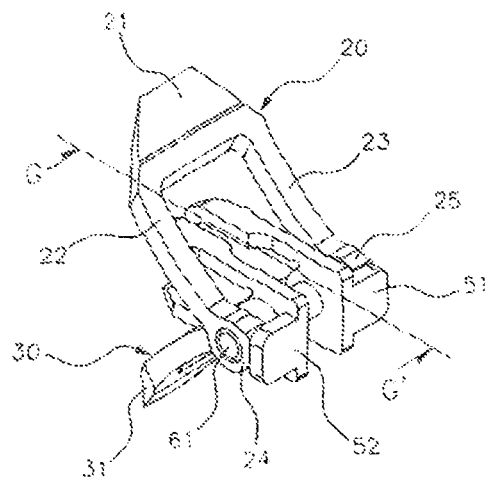
FIG. 10A is another perspective view illustrating a state in which the upper and lower spikes of the cage, in accordance with the embodiment of the present invention, are coupled to the clip, but shown in an alternate position.
Figure 10B:
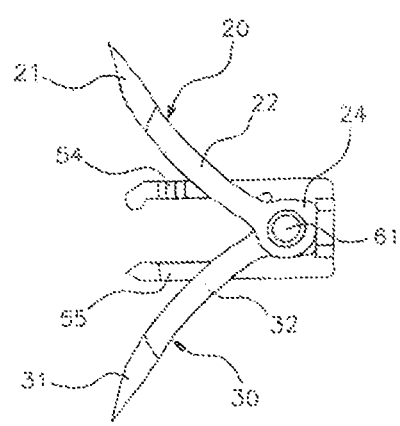
FIG. 10B is a cross-sectional view taken along the line G-G' in FIG. 10A.

Thus, the upper and lower spikes 20 and 30 coupled to the clip 50 are operated as illustrated in FIGS. 10A and 10B. More specifically, the upper blade 21 of the upper spike 20 is revolved upward and downward around the fastening holes 24 and 25 coupled to the clip 50, and the lower blade 31 of the lower spike 20 is revolved upward and downward around the fastening holes 34 and 35.

Figure 11A:
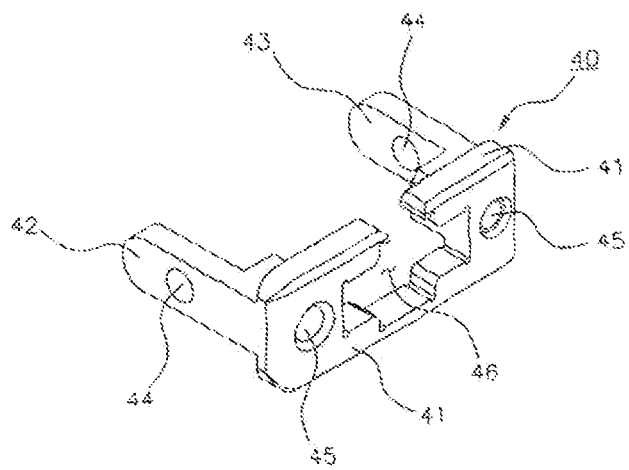
FIGS. 11A to 11C are detailed diagrams of a guide block of the cage in accordance with the embodiment of the present invention.
Figure 11B:
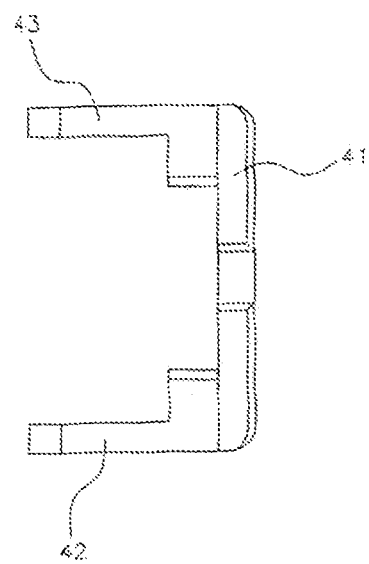
Figure 11C:
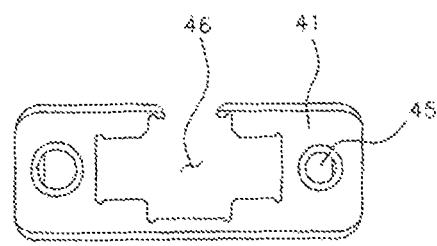

FIGS. 11A to 11C are detailed diagrams of the guide block of the cage in accordance with the embodiment of the present invention. FIG. 11A is a perspective view, FIG. 11B is a plan view, and FIG. 11C is a front view.

Referring to FIGS. 11A to 11C, the guide block 40 in accordance with the embodiment of the present invention is coupled to the main body 10 so as to guide the insertion of the clip 50, and includes a front plate 41, left and right bars 42 and 43, through-holes 44, and an entrance hole 46. The front plate 41 closes the front surface 103 of the main body 10. The left and right bars 42 and 43 are formed to extend from ends of both side surfaces of the front plate 41 to the rear side. The through-holes 44 are formed through the left and right bars 42 and 43, respectively, such that the guide block coupling pin 60 is inserted into the through-holes 44. The entrance hole 46 is formed in the center of the front plate 41 so as to provide an opening through which the clip 50 is inserted.

After the left and right bars 42 and 43 of the guide block 40 are inserted into the mounting grooves 151 formed in the left and right side surfaces 102 of the main body 10, the guide block coupling pin 60 is inserted into the through-hole 44 of the left bar 42 and fastened to the through-hole 44 of the right bar 43 through the insertion hole 120. Thus, the main body 10 and the guide block 40 are coupled to each other.

Furthermore, the guide block 40 has one or more insertion holes 45 formed on the front plate 41 thereof such that a coupling screw (not illustrated) fixed to a head 210 of the insertion mechanism 200 to be described below is inserted into the insertion hole 45.

The operation of the case 10 in accordance with the embodiment of the present invention will be described with reference to FIGS. 12A to 12D.

Figure 12A:
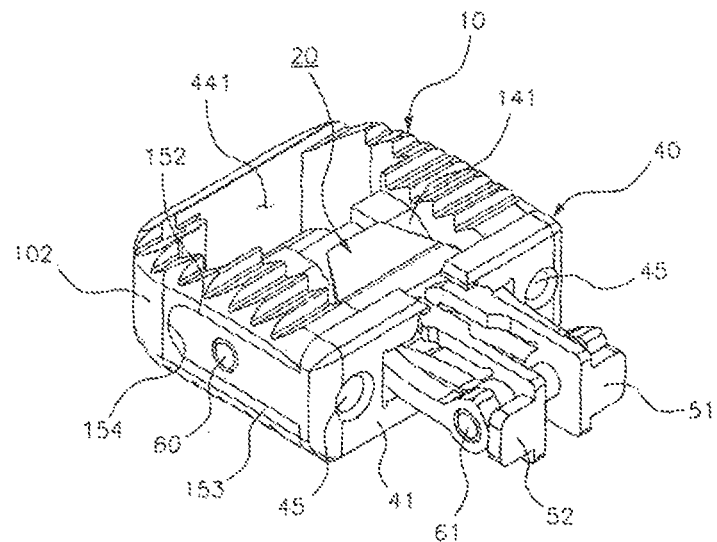
FIG. 12A to 12D are diagrams illustrating the operation state of the cage in accordance with the embodiment of the present invention, FIG. 12C being a cross-sectional view taken along the line H-H' of FIG. 12B.
Figure 12B:
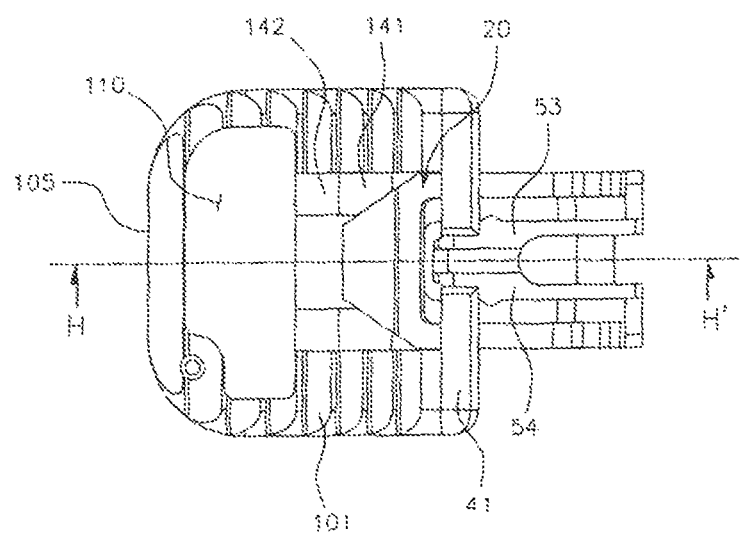
Figure 12C:
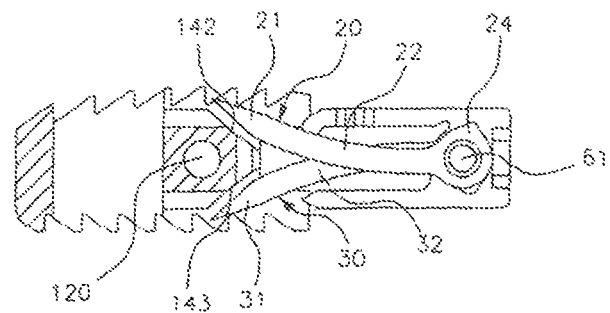
Figure 12D:
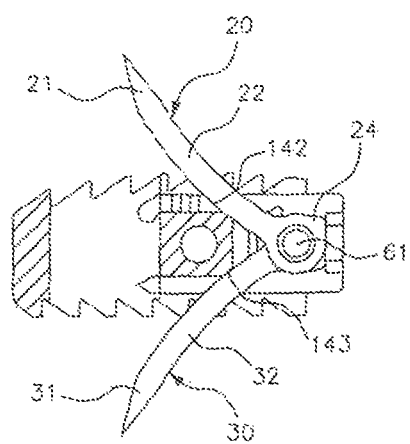

FIG. 12A is a perspective view illustrating that the clip is being inserted, FIG. 12B is a plan view illustrating that the clip is being inserted, FIG. 12C is a cross-sectional view taken along line H-H of FIG. 12B, illustrating that the spikes are folded, and FIG. 12D is a cross-sectional view illustrating that the spikes are unfolded.

The cage 10 in accordance with the embodiment of the present invention is operated in such a manner that the upper and lower spikes 20 and 30 are locked and fixed to upper and lower vertebral bodies of a cervical vertebral or spine at the part from which an intervertebral disc is removed.

First, as illustrated in FIGS. 12A and 12b, the main body 10 and the guide block 40 are coupled to each other, and the right and left retaining jaws 51 and 52 of the clip 50 coupled to the upper and lower spikes 20 and 30 are pushed by the insertion mechanism 200 to be described below. Then, the clip 50 is inserted into the main body 10 through the entrance hole 46 of the guide block 40.

In such a state where the clip 50 is inserted, the upper and lower spikes 20 and 30 are folded so as not to protrude to the outside of the top and bottom surfaces 101 and 104 of the main body 10, while the upper and lower blades 21 and 31 of the upper and lower spikes 20 and 30 reach entrances to the upper and lower inclined surfaces 142 and 143 of the inclined part 140 inside the main body 10, as illustrated in FIG. 12C.

Then, when the clip 50 is further pushed to the inside of the main body 10, the upper and lower spikes 20 and 30 coupled to the clip 50 are unfolded upward and downward as illustrated in FIG. 12D. More specifically, while guided along the upper and lower inclined surfaces 141 and 143 of the inclined part 140 formed in the main body 10, the upper and lower spikes 20 and 30 are moved upward and downward so as to protrude to the outside of the top and bottom surfaces 101 of the main body 10, until the base 57 of the clip 50 is locked to the protruding surface 146 formed in the center of the inclined part 140.

At this time, the right and left ribs 53 and 54 of the clip 50 are slid and mounted on the top plane surface 142 of the inclined part 140, and the lower rib 55 of the clip 50 is slid and mounted on the bottom plane surface 144 of the inclined part 140.

Thus, since the cage 1 in accordance with the embodiment of the present invention includes the upper and lower spikes to perform such an unfolding operation, it is possible to omit a complicated operation of fixing a plate through a screw in a small intervertebral space in the related art. Thus, the convenience of medical treatment and the stability of operation may be improved.

Figure 13A:
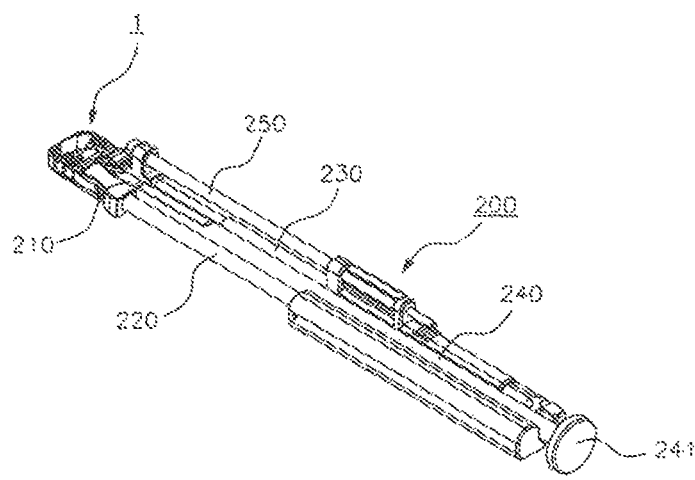
FIGS. 13A to 13D illustrate an insertion mechanism for inserting the cage in accordance with the embodiment of the present invention.
Figure 13B:
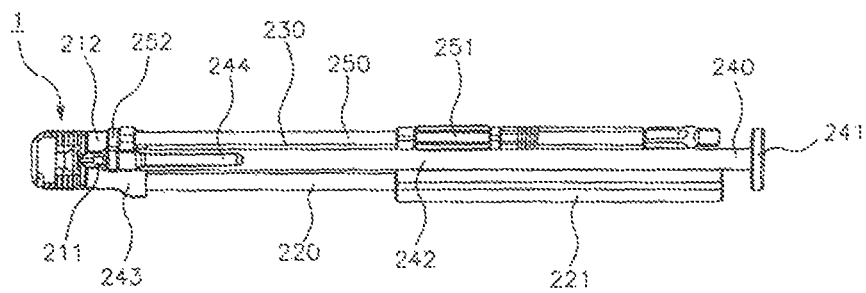
Figure 13C:
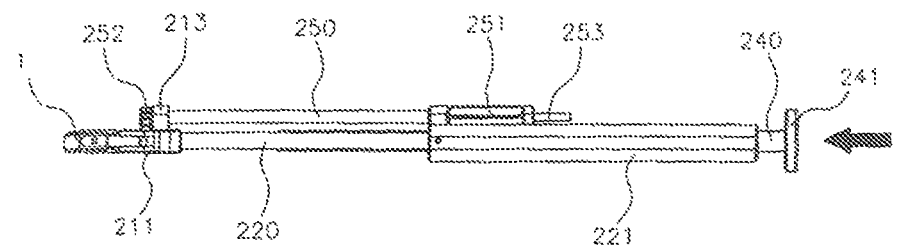

FIGS. 13A to 13C illustrate the insertion mechanism for inserting the cage in accordance with the embodiment of the present invention. FIG. 13A is a perspective view, FIG. 13B is a plan view, and FIG. 13C is a side view illustrating a state in which the spikes are folded.

The insertion mechanism 200 is used to more stably insert the clip 50 coupled to the upper and lower spikes 20 and 30 into the main body 10 of the cage 1.

Referring to FIGS. 13A to 13C, the insertion mechanism 200 for the cage 1 has a head 210 which is coupled to the guide block 40 through a coupling screw (not illustrated) inserted into the insertion hole 45 of the front plate 41 of the guide block 40.

The head 210 is formed in a hexahedral shape, and has a left side coupled to one side of a first lower support rod 220 and a right side coupled to one side of a second lower support rod 230.

Furthermore, a push stick 240 is positioned between the first and second lower support rods 220 and 230. The push stick 240 has a boss 243 formed at one end thereof so as to push the clip 50 into the main body 10.

Figure 13D:
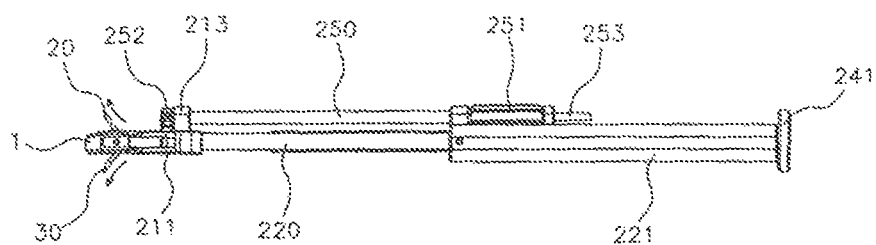

The push stick 240 includes a push plate 241, a rod body 242, and a coupling member 244. The push plate 241 is formed at the other end of the push stick 240, the rod body 242 is extended from the push plate 241, and the coupling member 244 connects the rod body 242 and the boss 243. When the push plate 241 is pushed forward, the boss 243 connected to the coupling member 244 is moved forward through the rod body 242 so as to insert the clip 50 into the main body 10 of the cage 1 as illustrated in FIG. 13D. Then, the upper and lower spikes 20 and 30 are unfolded to protrude to the outside of the top and bottom surfaces of the main body 10.

For such an operation, the head 210 includes a left head 211 coupled to the first lower support rod 220 and a right head 212 coupled to the second lower support rod 230, and the boss 243 of the push stick 240 is fastened between the left and right heads 211 and 212 so as to move forward or backward. The other end of the first lower support rod 220 and the other end of the second lower support rod 240 are inserted into a push stick guide 221 in which the rod body 242 of the push stick 240 is mounted.

The head 210 of the insertion mechanism 200 further includes an upper head 213 into which one end of the upper support rod 250 is inserted, and the other end of the upper support rod 250 is inserted into an upper support rod guide 251 formed at the top of the push guide 221. Furthermore, a support body 252 is attached to the one end of the upper support rod 250.

When the clip 50 is inserted, the upper support rod 250 is contacted with an upper vertebral body of a cervical vertebra or spine, into which the cage 1 is to be placed, thereby improving the stability of the insertion mechanism 200.

Figure 14:
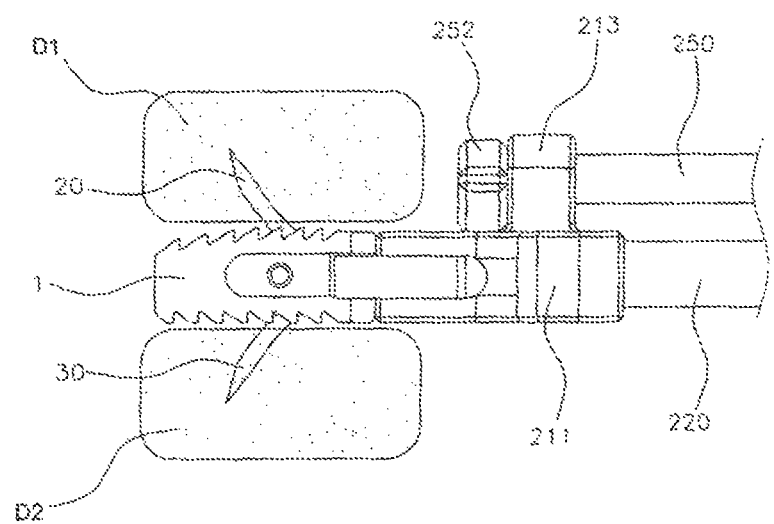
FIG. 14 is a diagram illustrating a state in which the cage in accordance with the embodiment of the present invention is placed.

FIG. 14 is a diagram illustrating a state in which the cage 10 in accordance with the embodiment of the present invention is placed. Referring to FIG. 14, the cage 1 is positioned between upper and lower vertebral bodies D1 and D2 of a cervical vertebra or spine, and the clip 50 is inserted into the main body 10 through the insertion mechanism 200 such that the upper and lower spikes 20 and 30 protrudes to the outside of the top and bottom surfaces 101 and 104 of the main body 10. Then, the pointed end surfaces of the upper and lower blades 21 and 31 at the ends of the spikes 20 and 30 are locked to the upper and lower vertebral bodies D1 and D2 positioned at the top and bottom of the cage 1 such that the cage 1 is fixed and locked between the upper and lower vertebral bodies D1 and D2.

During an actual procedure, the clip 50 is carefully and slowly inserted into the main body 10 while the push plate 241 formed at the other end of the push stick 240 is hit by a hammer for operation (not illustrated).

Thus, the upper and lower spikes 20 and 30 are positioned between the upper and lower vertebral bodies D1 and D2 so as to be reliably fixed to the inner rear sides of the upper and lower vertebral bodies D1 and D2. Thus, it is possible to significantly reduce the possibility that the screw or a part of the plate included in the conventional cages will interfere with the nerve tissue or blood tissue passing through the cervical vertebra or spine at the part from which the intervertebral disk was removed and in which the cage is installed.

While the present invention has been described in connection with the exemplary embodiments illustrated in the drawings, they are merely illustrative and the invention is not limited to these embodiments. It will be appreciated by a person having an ordinary skill in the art that various equivalent modifications and variations of the embodiments can be made without departing from the spirit and scope of the present invention. Therefore, the true technical scope of the present invention should be defined by the technical spirit of the appended claims.

What is claimed is:

1. A cage configured for placement between vertebral bodies of a cervical vertebra or spine, comprising:
   a main body formed in a hexahedral shape having a top surface, both side surfaces, a front surface, a bottom surface, and a rear surface;
   a clip operated to be inserted into the main body through the front surface;
   an upper spike coupled to the clip and unfolded to protrude to an outside of the top surface of the main body through the insertion of the clip into the main body;
   a lower spike coupled to the clip and unfolded to protrude to an outside of the bottom surface of the main body through the insertion of the clip into the main body;
   a clip coupling pin rotationally connecting the upper spike to the lower spike; and
   a guide block coupled to the main body so as to guide the insertion of the clip into the main body.

2. The cage according to claim 1, wherein the main body has a bone fusion hole formed through the top and bottom surfaces, a channel part is formed from the front surface to a central part of the main body so as to provide a space into which the clip is inserted, an inclined part is formed in the main body so as to guide the movement of the upper and lower spikes, and mounting grooves are formed at both side surfaces of the main body such that left and right bars of the guide block are mounted on the respective mounting grooves.

3. The cage according to claim 2, wherein the inclined part comprises:
   an upper inclined surface formed to guide the upward movement of the upper spike; and
   a lower inclined surface formed to guide the downward movement of the lower spike, a top plane surface is formed at an end of the upper inclined surface, and a bottom plane surface is formed at an end of the lower inclined surface.

4. The cage according to claim 2, wherein the upper spike comprises:
   an upper blade having an end to form a pointed end surface;
   arms formed at both sides of the upper blade and extended to be inclined downward; and
   fastening holes formed at ends of the respective arms such that the clip coupling pin is inserted into the fastening holes, and wherein the lower spike comprises:
   a lower blade having an end to form a pointed end surface;

arms formed at both sides of the lower blade and extended to be inclined upward; and fastening holes formed at ends of the respective arms such that the clip coupling pin is inserted into the fastening holes.

5. The cage according to claim 3, wherein the clip comprises:

right and left retaining jaws having a plate shape and formed at the front of a base;

right and left ribs formed at the rear top of the base so as to be slid and mounted on the top plane surface of the inclined part;

a lower rib formed at the rear bottom of the base so as to be slid and mounted on the bottom plane surface of the inclined part; and through-holes formed through the base of the clip, wherein the clip coupling pin is inserted into the through-holes.

6. The cage according to claim 5, wherein the inclined part has a protruding surface formed at connection between the upper and lower inclined surfaces, and when the clip is inserted into the main body, the protruding surface of the inclined part is locked to an inside of the base so as to stop the insertion of the clip.

7. The cage according to claim 2, wherein the guide block comprises:

a front plate having a plate shape and closing the front surface of the main body;

left and right bars extended from both ends of the front plate to a rear side;

through-holes formed through the left and right bars and, respectively, such that a guide block coupling pin is inserted into the through-holes; and an insertion hole formed in the center of the front plate so as to provide an opening through which the clip is inserted.

8. The cage according to claim 2, wherein saw-toothed bodies are formed on the top and bottom surfaces of the main body.

* * * * *